United States Patent
Carroll et al.

(10) Patent No.: US 9,932,594 B2
(45) Date of Patent: Apr. 3, 2018

(54) METHODS AND COMPOSITIONS FOR TREATING NEUROPATHIC PAIN

(71) Applicants: INSERM (Institut National de la Sante et de la Recherche Medicale), Paris (FR); Universite de Montpellier, Montpellier (FR)

(72) Inventors: Patrick Carroll, Montpellier (FR); Alexandre Pattyn, Montpellier (FR); Stephanie Venteo, Montpellier (FR)

(73) Assignees: INSERM (Institut National de la Sante et de la Recherche Medicale), Paris (FR); Universite de Montpellier, Montpellier (FR)

(*) Notice: Subject to any disclaimer, the term of this patent is extended or adjusted under 35 U.S.C. 154(b) by 0 days.

(21) Appl. No.: 15/324,118

(22) PCT Filed: Jul. 8, 2015

(86) PCT No.: PCT/EP2015/065545
§ 371 (c)(1),
(2) Date: Jan. 5, 2017

(87) PCT Pub. No.: WO2016/005422
PCT Pub. Date: Jan. 14, 2016

(65) Prior Publication Data
US 2017/0183662 A1 Jun. 29, 2017

(30) Foreign Application Priority Data
Jul. 9, 2014 (EP) .................. 14306114.1

(51) Int. Cl.
| | |
|---|---|
| A61K 48/00 | (2006.01) |
| C12N 15/11 | (2006.01) |
| C07H 21/02 | (2006.01) |
| C07H 21/04 | (2006.01) |
| C12N 15/113 | (2010.01) |

(52) U.S. Cl.
CPC ...... *C12N 15/1138* (2013.01); *C12N 2310/14* (2013.01); *C12N 2310/531* (2013.01)

(58) Field of Classification Search
USPC .......................................... 514/44; 536/24.5
See application file for complete search history.

(56) References Cited

PUBLICATIONS

Gegelashvilli et al. Neurochemistry International, 2007 vol. 50:916-920.*
Wetzel et al. J Biol Chem, 2004 vol. 279:41750-41757.*
Venteo et al.; "Regulation of the Na,K-ATPase Gamma-Subunit FXYD2 by Runx1 and Ret Signaling in Normal and Insured Non-Peptidergic Nociceptive Sensory Neurons"; PLOS One, vol. 7, No. 1, Jan. 13, 2012, entire article.

(Continued)

*Primary Examiner* — Terra C Gibbs
(74) *Attorney, Agent, or Firm* — Whitham, Curtis & Cook, P.C.

(57) ABSTRACT

The present invention relates to an inhibitor of FXYD2 gene expression for use in a method for treating neuropathic pain in a patient in need thereof. The invention also relates to a pharmaceutical composition comprising an inhibitor of FXYD2 gene expression, wherein said pharmaceutical composition is formulated for a direct administration into the peripheral nervous system (PNS) of a patient (e.g., formulated for intrathecal administration).

7 Claims, 3 Drawing Sheets

Mechanical withdrawal threshold

(56) References Cited

PUBLICATIONS

Figure 1:
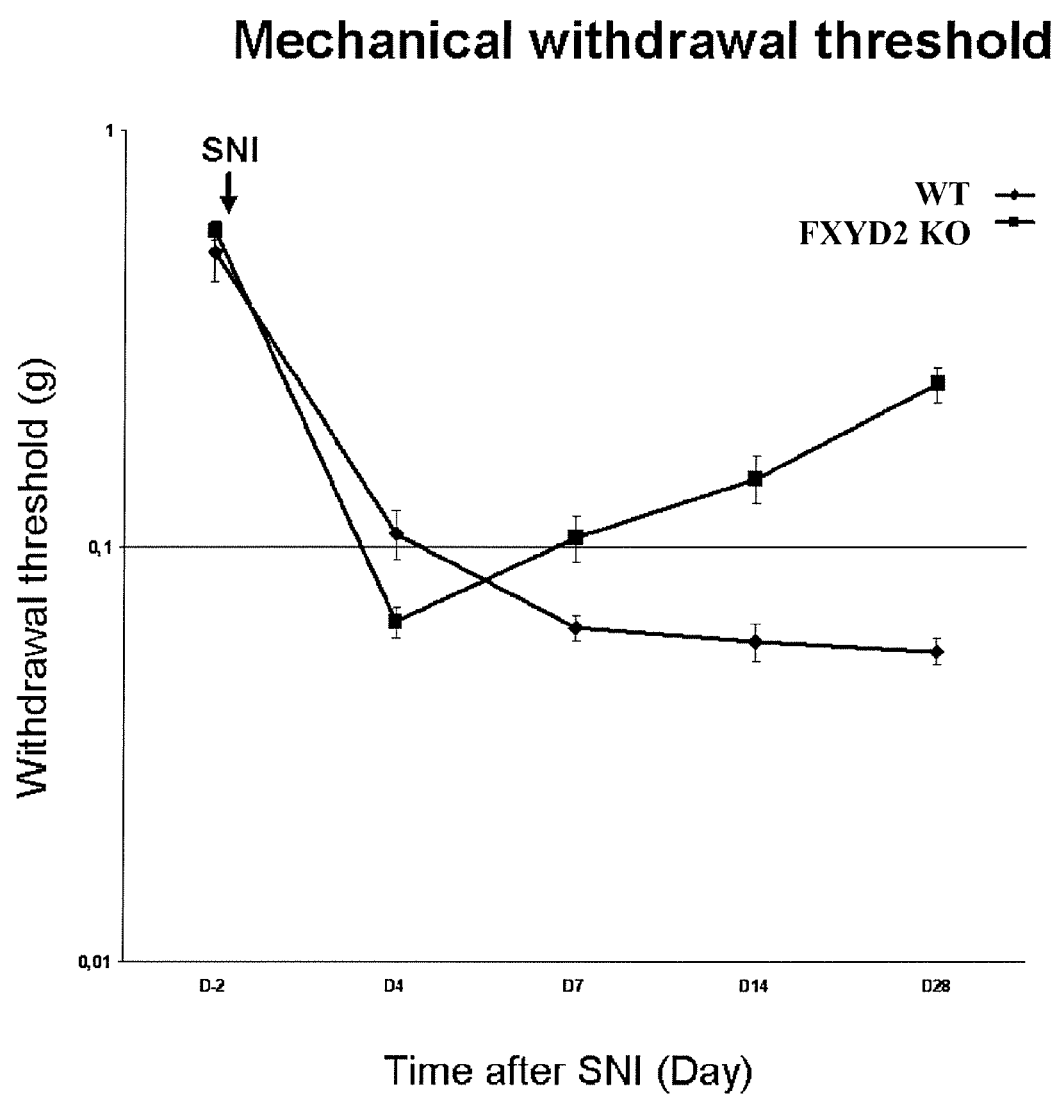

Boucher et al.; "Potent Analgesic Effects of GDNF in Neuropathic Pain States"; Science, vol. 290, No. 5489, Oct. 6, 2000, pp. 124-127.
Wang et al.; "Glial Cell Line-Derived Neurotrophic Factor Normalizes Neurochemical Changes in Injured Dorsal Root Ganglion Neurons and Prevents the Expression of Experimental Neuropathic Pain"; Neuroscience, vol. 121, No. 3, Oct. 1, 2003, pp. 815-824.
Dray; "Neuropathic pain: emerging treatments"; British Journal of Anaesthesia, vol. 101, No. 1, Apr. 19, 2008, pp. 48-58.
Sah et al.; "Neurotrophic Factors as Novel Therapeutics for Neuropathic Pain"; Nature Reviews/Drug Discovery, vol. 2, Jan. 1, 2003, pp. 460-472.
*Homo sapiens* FXYD domain containing ion transport regulator 2 (FXYD2), transcript variant b, mRNA, NCBI Reference Sequence: NM_021603.3.
*Homo sapiens* FXYD domain containing ion transport regulator 2 (FXYD2), transcript variant a, mRNA, NCBI Reference Sequence: NM_001680.4.

\* cited by examiner

SEQUENCE LISTING

```
<160> NUMBER OF SEQ ID NOS: 5

<210> SEQ ID NO 1
<211> LENGTH: 20
<212> TYPE: RNA
<213> ORGANISM: Artificial
<220> FEATURE:
<223> OTHER INFORMATION: Synthetic siRNA directed against the rat Fxyd2
      mRNA

<400> SEQUENCE: 1
aaucccuucg aguaugauuu                                                     20

<210> SEQ ID NO 2
<211> LENGTH: 21
<212> TYPE: RNA
<213> ORGANISM: Artificial
<220> FEATURE:
<223> OTHER INFORMATION: Synthetic human FXYD2 siRNA

<400> SEQUENCE: 2
uaagaagcgc aggcaaauca a                                                   21

<210> SEQ ID NO 3
<211> LENGTH: 19
<212> TYPE: RNA
<213> ORGANISM: Artificial
<220> FEATURE:
<223> OTHER INFORMATION: Synthetic Human FXYD2 siRNA

<400> SEQUENCE: 3
gauuugccug cgcuucuua                                                      19

<210> SEQ ID NO 4
<211> LENGTH: 584
<212> TYPE: DNA
<213> ORGANISM: Homo sapiens

<400> SEQUENCE: 4
agacactctc caaaaagcag agacagcagg aagaggggag tggaggcagc ccattcacct         60
```

```
ggggaaatga ctgggttgtc gatggacggt ggcggcagcc ccaaggggga cgtggacccg     120
ttctactatg actatgagac cgttcgcaat ggggcctga tcttcgctgg actggccttc      180
atcgtggggc tcctcatcct cctcagcaga agattccgct gtgggggcaa taagaagcgc     240
aggcaaatca atgaagatga gccgtaacag cagcctcggc ggtgccaccc actgcactgg     300
ggccagctgg gaagccaagc atggccctgc ctctggcgcc tccccttctt ccctgggctt     360
tagacctttg tccccgtcac tgccagcgct tgggctgaag gaagctccag actcaatgtg     420 accccaggt ggcatcgcca actcctgcct cgtgccacct catgcttata ataaagccgg      480
cgtcagagac cgctgcttcc ctcacctgcc tgcctgtctc cctcctctgt caccaccagc    540
ctctccaagc tcaagtacaa atacagccgg gaaaaaaaaa aaaa                     584

<210> SEQ ID NO 5
<211> LENGTH: 591
<212> TYPE: DNA
<213> ORGANISM: Homo sapiens

<400> SEQUENCE: 5
gccactctcc atccaggccc caggcaagca gcacctccct gctctcctgc actcctggac      60
acaaccagca gctcctgcca tggacaggtg gtacctgggc ggcagcccca aggggacgt     120 ggacccgttc tactatgact atgagaccgt tcgcaatggg ggcctgatct tcgctggact    180
ggccttcatc gtggggctcc tcatcctcct cagcagaaga ttccgctgtg ggggcaataa    240
gaagcgcagg caaatcaatg aagatgagcc gtaacagcag cctcggcggt gccacccact    300
gcactggggc cagctgggaa gccaagcatg gccctgcctc tggcgcctcc ccttcttccc    360
tgggctttag acctttgtcc ccgtcactgc cagcgcttgg gctgaaggaa gctccagact    420
caatgtgacc cccaggtggc atcgccaact cctgcctcgt gccacctcat gcttataata    480
aagccggcgt cagagaccgc tgcttccctc acctgcctgc ctgtctccct cctctgtcac    540
caccagcctc tccaagctca agtacaaata cagccgggaa aaaaaaaa a               591
```

METHODS AND COMPOSITIONS FOR TREATING NEUROPATHIC PAIN

FIELD OF THE INVENTION

The invention is in the field of neurology. More particularly, the invention provides methods and compositions comprising an inhibitor of FXYD2 gene expression for treating neuropathic pain. Also provided herein are methods of administering the composition of the invention by intrathecal injection in a patient in need thereof.

BACKGROUND OF THE INVENTION

Pain is generally divided into nociceptive and neuropathic pain. Nociceptive pain stems from neural pathways in response to tissue damaging or potentially tissue damaging signals, and includes inflammatory pain. Neuropathic pain tends to relate to dysfunctions within the nervous system. Unfortunately, agents that treat one kind of pain do not necessarily treat the other. Neuropathic pain is distinguished from inflammatory pain in that it is not mediated by arachidonic acid, cyclooxygenases and prostaglandins. Therefore, neuropathic pain is not reduced or alleviated by non-steroidal anti-inflammatory agents, e.g., inhibitors of cyclooxygenases ("COX"), including selective COX-2 inhibitors.

Until today, the pharmacological agents that have most commonly been shown to effectively block neuropathic pain are tricyclic anti-depressants (TCAs). However these agents are not effective at all in some patients and are only partially effective in others. TCAs have many disadvantages well known in the field. Since neuropathic pain is a debilitating and hard to treat condition, however, TCAs have been used despite their disadvantages in the absence of agents with less adverse effects.

Therefore the therapy of neuropathic pain is an unmet and growing clinical need.

It was recently shown that FXYD2, which encodes the gamma-subunit of the Na,K-ATPase reported so far to be mainly expressed in the kidney, is induced in the mouse DRGs at postnatal stages where it is restricted specifically to the TrkB-expressing mechanoceptive and Ret-positive/IB4-binding non-peptidergic nociceptive neurons. Accordingly, FXYD2 was considered as a novel specific marker restricted exclusively to said mechanoreceptors and nociceptors of primary somato-sensory neurons (Ventéo et al, 2012).

SUMMARY OF THE INVENTION

In a first aspect, the invention relates to an inhibitor of FXYD2 gene expression for use in a method for treating neuropathic pain in a patient in need thereof.

In a second aspect, the invention relates to a pharmaceutical composition comprising an inhibitor of FXYD2 gene expression and a pharmaceutically acceptable carrier, wherein said pharmaceutical composition is formulated for a direct administration into the peripheral central nervous system of a patient.

In a third aspect, the invention relates to a pharmaceutical composition comprising an inhibitor of FXYD2 gene expression for use in a method for treating neuropathic pain in a patient in need thereof

DETAILED DESCRIPTION OF THE INVENTION

The invention is based on experimental models of neuropathic pain in two different species (mouse and rat) and using two different methods to manipulate Fxyd2 expression (gene mutation and siRNA) showing that Fxyd2 function is necessary for the full expression of neuropathic pain behavior. In both experimental models, loss or decrease of Fxyd2 function caused dramatic reduction of the pain behavior. Such results suggest that Fxyd2 in somatosensory neurons is a new therapeutic target for treating neuropathic pain.

Therapeutic Methods and Uses

In a first aspect, the invention relates to an inhibitor of FXYD2 gene expression for use in a method for treating neuropathic pain in a patient in need thereof.

As used herein, the term "FXYD domain containing ion transport regulator 2" (also known as "FXYD2") has its general meaning in the art and refers to the gamma-subunit of the Na,K-ATPase. The term includes naturally occurring FXYD2 variants and modified forms thereof. The naturally occurring human FXYD2 gene has a nucleotide sequence as shown in Genbank Accession number NM_001680.4 (a variant) and NM_021603.3 (b variant).

As used herein, the term "inhibitor of gene expression" refers to a natural or synthetic compound that has a biological effect to inhibit the expression of a gene.

In a preferred embodiment of the invention, said inhibitor of gene expression is a siRNA, a shRNA, an antisense oligonucleotide or a ribozyme.

Inhibitors of gene expression for use in the invention may be based on antisense oligonucleotide constructs. Anti-sense oligonucleotides, including anti-sense RNA molecules and anti-sense DNA molecules, would act to directly block the translation of the targeted mRNA by binding thereto and thus preventing protein translation or increasing mRNA degradation, thus decreasing the level of the targeted protein (i.e. FXYD2), and thus activity, in a cell. For example, antisense oligonucleotides of at least about 15 bases and complementary to unique regions of the mRNA transcript sequence encoding the target protein can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of gene expression for use in the present invention. Gene expression can be reduced by contacting the subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). Short hairpin RNAs (siRNAs) can also function as inhibitors of gene expression for use in the invention.

Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the targeted mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Antisense oligonucleotides, siRNAs, shRNAs and ribozymes useful as inhibitors of gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol.7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SAMBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pRC/CMV and SV40. Other plasmids are well known to those of ordinary skill in the art. Additionally, plasmids may be custom designed using restriction enzymes and ligation reactions to remove and add specific fragments of DNA. The plasmids may be given in an aqueous solution, dried onto gold particles or in association with another DNA delivery system including but not limited to liposomes, dendrimers and microencapsulation.

Examples of inhibitors of FXYD2 gene expression include FXYD2 siRNA such as the "ON-TARGET plus" siRNA directed against the rat Fxyd2 mRNA (ref. TMOSLR-005187) was purchased from Thermo Scientific which is represented by the sense sequence 5'-AAUC-CCUUCGAGUAUGAUUU-3' (SEQ ID NO: 1).

In one embodiment, said FXYD2 siRNA is directed against the human FXYD2 gene. Said siRNA is for example human FXYD2 siRNAs described in Gegelashvili et al., 2007 which is incorporated herein by reference and which are represented by the
 sense sequence—5'-UAAGAAGCGCAGGCAAAU-CAA-3' (SEQ ID NO: 2), and antisense sequence—5'-GAUUUGCCUGCGCUUC-UUA-3' (SEQ ID NO: 3).

In a particular embodiment, human FXYD2 siRNAs contain two nucleotide overhangs on their 3' end (e.g. 2 deoxythymidines (dT-dT)).

Other human FXYD2 siRNAs are commercilay available and include for instance those purchased by Origene (Cat. no. SR300342), Santa Cruz (Cat. no. SC-42422), Dharmacon (L-017391-00; LU-017391-00; LQ-017391-00; J-017391-05; J-017391-06; J-017391-07; J-017391-08) and Life technologies (Cat. no. 1299001).

As used herein, the term "neuropathic pain" refers to pain resulting from a pathology in the nervous system. Notable features of neuropathic pain include (1) widespread pain not otherwise explainable; (2) evidence of sensory deficit; (3) burning pain; (4) pain to light stroking of the skin (allodynia); and (5) enhanced stimulus-dependent pain (hyperalgesia) and (6) attacks of pain without seeming provocation (stimulus-independent pain). Neuropathic pain originates from a lesion of the nervous system. Any of a number of disease conditions or injuries can be the underlying cause of neuropathic pain. For example, the patient may be suffering from a metabolic disease g., diabetic neuropathy), an autoimmune disease (e.g., multiple sclerosis), a viral infection (e.g., shingles and sequelae, postherpetic neuralgia), vascular disease (e.g., stroke), trauma and/or cancer.

In one embodiment, the neuropathic pain is peripheral neuropathic pain. In another embodiment, the neuropathic pain is central neuropathic pain.

In one embodiment, the neuropathic pain is selected from the group consisting of post-herpetic neuralgia, trigeminal neuralgia, focal peripheral nerve injury, and anesthesia dolorosa, central pain due to stroke or mass lesion, spinal cord injury, or multiple sclerosis, and peripheral neuropathy due to diabetes, HIV, or chemotherapy, post-operative pain and post-amputation pain.

As used herein, the term "patient" refers to a mammal such as a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

As used herein, the term "patient in need thereof" refers to a patient is suffering from peripheral neuropathic pain, for example, as a result of a disease condition including acute and chronic inflammatory demyelinating polyradiculoneuropathy; alcoholic polyneuropathy; chemotherapy-induced polyneuropathy; complex regional pain syndrome; entrapment neuropathies (e.g., carpal tunnel syndrome); HfV sensory neuropathy: iatrogenic neuralgias (e.g., postmastectomy pain or postthoracotomy pain); idiopathic sensory neuropathy; nerve compression or infiltration by tumor; nutritional deficiency-related neuropathies; painful diabetic neuropathy; phantom limb pain; postherpetic neuralgia; postradiation plexopathy; radiculopathy (cervical, thoracic, or lumbosacral); toxic exposure-related neuropathies; tic douloureux (trigeminal neuralgia); and/or posttraumatic neuralgias.

In one embodiment, the patient in need thereof may be subject to suffering neuropathic pain chronically or intermittently. In another embodiment, the patient in need thereof may or may not be exhibiting or experiencing symptoms of neuropathic pain at the time of treatment.

In a another aspect, the invention relates to a method for treating neuropathic pain in a patient in need thereof, comprising a step of administering a therapeutically effective amount of an inhibitor of FXYD2 gene expression in a manner such that the inhibitor is directly administered into the peripheral nervous system of said patient.

The invention also relates to a method for treating neuropathic pain in a patient in need thereof, comprising a step of administering intrathecally a therapeutically effective amount of an inhibitor of FXYD2 gene expression in said patient.

The inhibitor of the invention may be administered in the form of a pharmaceutical composition, as defined below. Preferably, said inhibitor in a therapeutically effective amount. By a "therapeutically effective amount" is meant a sufficient amount of the agent to treat neuropathic pain at a reasonable benefit/risk ratio applicable to any medical treatment. For example, a "therapeutically effective amount of the active agent" to a patient is an amount of the active agent that induces, ameliorates or causes an improvement in the pathological symptoms, disease progression, or physical conditions associated with the disease affecting the patient. The present methods find use in treating, i.e., reducing, relieving, alleviating, ameliorating, or inhibiting neuropathic pain in a patient in need thereof. The term "reduce", "inhibit", "relieve", "alleviate" refer to the detectable decrease in symptoms of neuropathic pain, as determined by a trained clinical observer. A reduction in neuropathic pain can be measured by self-assessment (e.g., by reporting of the patient), by applying pain measurement assays well known in the art (e.g., tests for hyperalgesia and/or allodynia), and/or objectively (e.g., using functional magnetic resonance imaging or f-MRI). Determination of a reduction of neuropathic pain can be made by comparing patient status before and after treatment.

Pharmaceutical Compositions

In a second aspect, the invention relates to a pharmaceutical composition comprising an inhibitor of FXYD2 gene expression and a pharmaceutically acceptable carrier, wherein said pharmaceutical composition is formulated for a direct administration into the peripheral nervous system (PNS) of a patient.

The pharmaceutical compositions and related methods of the invention are useful for delivering an inhibitor of FXYD2 gene expression to the CNS of a patient (e.g., intrathecally, intraventricularly or intracisternally) and for the treatment of neuropathic pain.

In one embodiment, the pharmaceutical composition comprising an inhibitor of FXYD2 gene expression and a pharmaceutically acceptable carrier is formulated for intrathecal administration.

As used herein, the terms "pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In general the pharmaceutical compositions described herein may be prepared in a conventional manner using conventional excipients or carriers that are well known in the art.

As used herein, the terms "intrathecal administration" or "intrathecal injection" refer to an injection into the spinal canal (intrathecal space surrounding the spinal cord). Various techniques may be used including, without limitation, lateral cerebroventricular injection through a burrhole or cisternal or lumbar puncture or the like.

In one embodiment, intrathecal administration is used to deliver an inhibitor of FXYD2 gene expression into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al, Cancer Drug Delivery, 1: 169-179, the contents of which are incorporated herein by reference.

According to the invention, an inhibitor of FXYD2 gene expression may be injected at any region surrounding the spinal canal.

In some embodiments, the inhibitor of FXYD2 gene expression is injected into the lumbar area or the cisterna magna or intraventricularly into a cerebral ventricle space.

As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar intrathecal delivery" or "lumbar intrathecal administration."

The term "cisterna magna" refers to the space around and below the cerebellum via the opening between the skull and the top of the spine. Typically, intrathecal injection via cisterna magna is also referred to as "cisterna magna delivery."

The term "cerebral ventricle" refers to the cavities in the brain that are continuous with the central canal of the spinal cord. Typically, injections via the cerebral ventricle cavities are referred to as "intraventricular Cerebral (ICV) delivery".

In one embodiment, "intrathecal administration" or "intrathecal delivery" according to the invention refers to lumbar intrathecal administration or delivery, for example, delivered between the third and fourth lumbar (lower back) vertebrae and, more inclusively, the L2-S1 region of the spine. It is contemplated that lumbar intrathecal administration or delivery distinguishes over cisterna magna delivery in that lumbar intrathecal administration or delivery according to our invention provides better and more effective delivery to the distal spinal canal, while cisterna magna delivery, among other things, typically does not deliver well to the distal spinal canal.

Various devices may be used for intrathecal delivery according to the invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

Relative to intravenous administration, a single dose volume suitable for intrathecal administration is typically small. Typically, intrathecal delivery according to the invention maintains the balance of the composition of the CSF as well as the intracranial pressure of the subject. In some embodiments, intrathecal delivery is performed absent the corresponding removal of CSF from a patient. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before intrathecal administration. In those cases, a suitable single dose volume may be e.g., more than about 3 ml, 4 ml, 5 ml, 6 ml, 7 ml, 8 ml, 9 ml or 10 ml.

Various other devices may be used to effect intrathecal administration of a therapeutic composition. For example, pharmaceutical compositions comprising an inhibitor of FXYD2 gene expression may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses For injection, pharmaceutical compositions of the invention can be formulated in liquid solutions. In addition, the inhibitor FXYD2 gene expression may be formulated in solid form and re-dissolved or suspended immediately prior to use. Lyophilized forms are also included. The injection can be, for example, in the form of a bolus injection or continuous infusion (e.g., using infusion pumps) of the enzyme.

In a third aspect, the invention relates to a pharmaceutical composition comprising an inhibitor of FXYD2 gene expression for use in a method for treating neuropathic pain in a patient in need thereof.

It will be understood that the total daily usage of the inhibitor of the invention or the pharmaceutical composition comprising thereof will be decided by the attending physician within the scope of sound medical judgment. The specific therapeutically effective dose level for any particular patient will depend upon a variety of factors including the disorder being treated and the severity of the disorder; activity of the specific inhibitor employed; the specific pharmaceutical composition employed, the age, body weight, general health, sex and diet of the subject; the time of administration, route of administration, and rate of excretion of the specific inhibitor employed; the duration of the treatment; drugs used in combination or coincidental with the specific inhibitor employed; and like factors well known in the medical arts. For example, it is well within the skill of the art to start doses of the inhibitor at levels lower than those required to achieve the desired therapeutic effect and to gradually increase the dosage until the desired effect is achieved. However, the daily dosage of the inhibitor may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the agent for the symptomatic adjustment of the dosage to the subject to be treated. A medicament typically contains from about 0.01 mg to about 500 mg of the active ingredient, preferably from 1 mg to about 100 mg of the active ingredient. An effective amount of the active ingredient is ordinarily supplied at a dosage level from 0.0002 mg/kg to about 20 mg/kg of body weight per day, especially from about 0.001 mg/kg to 7 mg/kg of body weight per day.

The invention will be further illustrated by the following figures and examples. However, these examples and figures should not be interpreted in any way as limiting the scope of the present invention.

FIGURES

FIG. 1: Comparison of mechanical hypersensitivity between WT and Fxyd2 KO mice in SNI model of neuropathic pain. Von Frey testing on WT and Fxyd2 KO mice age 8-10 weeks old was performed 2 days prior to SNI operation and repeatedly following surgery. Six animals were included in each group. Four days after surgery the animals developed clear mechanical hypersensitivity that was maintained up to 28 days post SNI, no significant change occurred in wild-type (WT) mice. In Fxyd2 null mutant mice (KO) mechanical withdrawal threshold increased dramatically between days 4 and 28 post-SNI.

Figure 2:
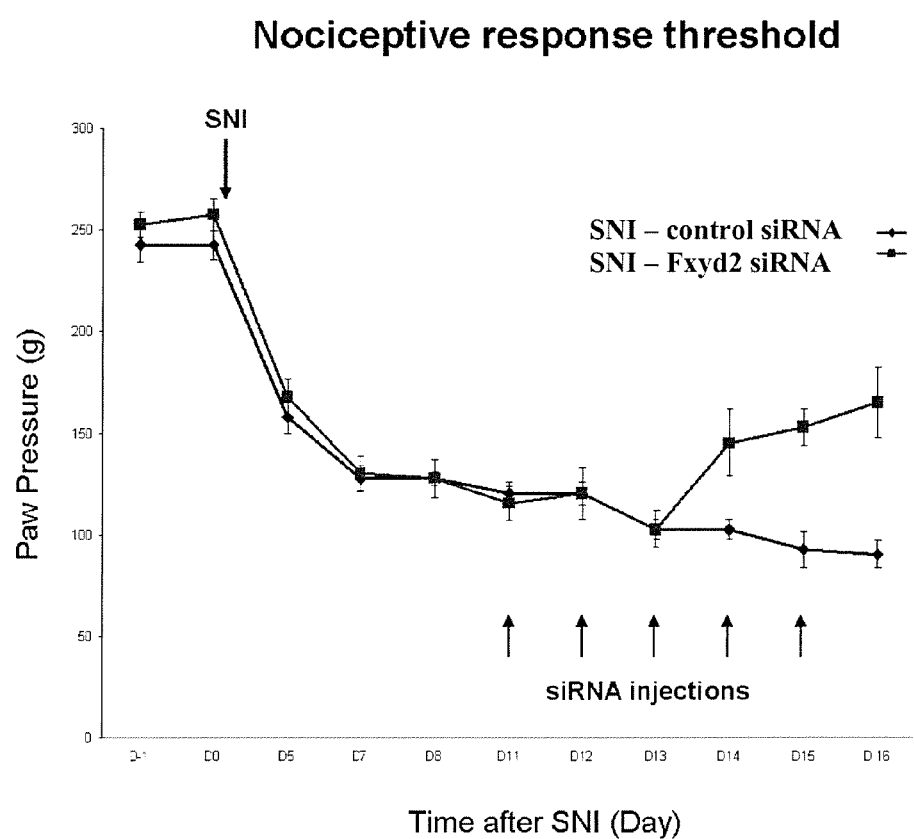

FIG. 2: Effect of intrathecal injection of Fxyd2 siRNA in an experimental model of neuropathic pain in rats. Baseline nocicepive threshold was evaluated on rats aged 4-5 weeks with the paw pressure vocalization test (Randall-Stilletto test) one day before and the day of SNI operation and repeatedly following surgery. Two groups of 6 rats were tested: SNI-control siRNA and SNI-Fxyd2 siRNA. After establishment of reduced nociceptive threshold (day 5 to 8), Fxyd2 or control siRNA were injected intrathecally on indicated days (arrows). On day 16, we observed a dramatic increase in nociceptive threshold to 165 g in SNI-Fxyd2 siRNA animals, at which time the SNI-control siRNA animals levels were 90.0 g.

Figure 3:
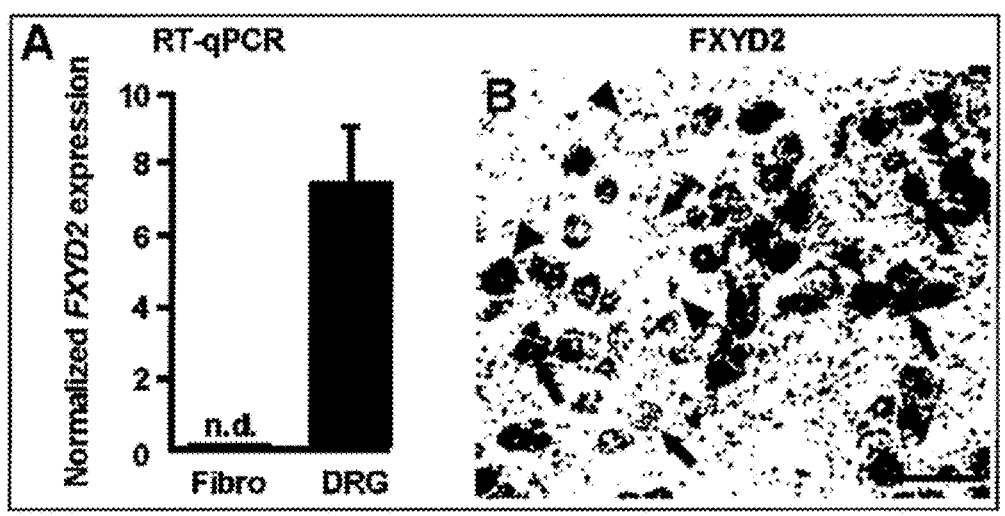

FIG. 3: Conserved restricted expression of FXYD2 in human DRGs.

(A) RT-qPCR analysis of FXYD2 expression on human fibroblasts and human DRGs samples revealing specific detection of FXYD2 in the DRGs (n=3 replicates).

(B) Immunohistochemistry on human lumbar DRG transverse sections using an anti-FXYD2 antibody. FXYD2 is detected in subpopulations of sensory neurons of small- (black arrows) and medium-diameters (black arrowheads). The two arrows and two arrowheads (in the middle) point to FXYD2-negative small and large diameter neurons, respectively.

EXAMPLES

Example 1

Material & Methods
Animals and Surgery:
All experiments were approved by the Direction Départementale des Services Vétérinaires de l'Hérault (Certificate of Animal Experimentation n° 34-376,17 February 2009) and the guidelines of the International Association for the Study of Pain (IASP).

Eight-to-ten week-old C57BL/6 male mice (Charles River, France) or Fxyd2 null mice (Jones et al, 2005) were housed with a 12/12 dark/light cycle and ad libitum access to water and food (n=6 in each group). Male Sprague-Dawley rats (Janvier), weighing 200 to 250 g (4 to 5 weeks of age) at the beginning of the experiments, were used.

Animals were deeply anesthetized with Ketamine-Xylasine (respectively 100 mg/kg and 10 mg/kg), and unilateral spared nerve injury (SNI) surgery was performed (Decosterd and Woolf, 2000). Briefly, the left hindlimb was immobilized in a lateral position and slightly elevated. Skin incision was made at mid-thigh level using the femur as a landmark, and muscle layers were separated to bring out the sciatic nerve and its three branches (sural, common peroneal, and tibial nerves). Both tibial and common peroneal nerves were tightly ligated with a 6.0 silk thread (Ethicon, Johnson, and Johnson Intl, Brussels, Belgium), transected together and a 1-2 mm section of the two nerves was removed. The sural branch was carefully preserved by avoiding any nerve stretch or contact with surgical tools. The muscle layer was closed by careful apposition and skin sutured with vicryl 4.0 threads. A subcutaneous injection of NaCl 0.9% (10 ml/1 kg) was finally performed to prevent for dehydratation.

Behavioral Testing on Mice:

Mechanical sensitivity was assessed by placing animals on an elevated wire mesh grid and stimulating the hind paw with Von Frey hairs by using the up-down paradigm (Chaplan et al, 1994). The left hindpaw was tested twice at 30 min intervals.

The schedule of the experiment was as follows. After testing for baseline mechanical sensitivity on two occasions separated by at least 24 h, mice were subjected to surgery (SNI model). Note that, as this model spared the sural territory, von Frey stimuli were aimed at the lateral aspect of the hindpaw during the baseline and post-operative measurements. Mice were then tested for mechanical sensitivity on postoperative days 4, 7, 14 and 28.

Intrathecal siRNA Injection in Rats:

An "ON-TARGET plus" siRNA directed against the rat Fxyd2 mRNA (ref. TMOSLR-005187) was purchased from Thermo Scientific. The sequence was as follows: sense sequence 5'-AAUCCCUUCGAGUAUGAUUU-3' (SEQ ID NO: 1). The siGENOME Non-targeting siRNA #2 (Ref. D-001210-02-20 Thermo Scientific) was used a negative control.

Rats were daily intrathecally injected under brief isoflurane anesthesia with 2 µg of Fxyd2 or control siRNA in Exgen transfection reagent (Euromedex ref. ET0250) in a volume of 20 µl. The transfection mix was prepared as follows: 10 µl of siRNA solution containing 50 µg was mixed with 240 µl of 5% glucose solution in water. Exgen500 transfection reagent (9 µl) was separately added to 241 µl of glucose solution and mixed. After combining the 2 solutions, they were mixed by vortexing and left for 10' at room temperature before intrathecal injections.

Behavioural Testing on Rats:

Male Sprague-Dawley rats (Janvier), weighing 200 to 250 g (4 to 5 weeks of age) at the beginning of the experiments, were used. They were housed three per cage under standard conditions of light and temperature, for at least one week before and throughout the whole experimental period. Commercial chow pellets and tap water were available ad libitum. Animals were acclimatized to the animal care unit for a week. During the seven days before the experiment, rats were weighed daily and placed in the test room for one hour. Mechanical hyperalgesia (painful response to normally innocuous tactile stimuli) was evaluated the day before and the day of surgery (D-1 and D0) and on each day of the experiment. Nociceptive thresholds were measured using the Randall-Siletto paw pressure test as previously described in Kayser V et al. (1990). Briefly, an incremental pressure was applied to the hindpaw by means of an automated gauge (Ugo Basile) and the nociceptive threshold was estimated by the time of vocalization, upon which pressure was stopped and the threshold (weight in grams) was noted. A cutoff of 600 g was used to avoid causing undue distress.

Results

Mice lacking the Fxyd2 gene function fail to maintain pain behavior in the SNI experimental model of neuropathic pain. To test the role of Fxyd2 in neuropathic pain, 8-10 weeks old male wild-type (WT) mice and mice carrying a null mutation in the Fxyd2 gene (Jones et al, 1995) underwent unilateral spared nerve injury (SNI) (Decosterd and Woolf, 2000). Mechanical sensitivity was assessed by placing animals on an elevated wire mesh grid and stimulating the hind paw with Von Frey hairs by using the up-down paradigm (Chaplan et al, 1994). Von Frey testing on WT and Fxyd2 null mutant mice was performed 2 days prior to SNI operation and at 4, 7, 14 and 28 days following surgery (FIG. 1). Four days post-surgery, both groups of animals had developed clear mechanical hypersensitivity. From day 4 at day 28 post SNI, WT mice maintained their hypersensitivity to mechanical stimuli as expected. However, in Fxyd2 null mutant mice, the mechanical withdrawal threshold increased dramatically between post-surgery days 7 and 28. Three conclusions can be drawn from these results. First, the nociceptive threshold in naïve Fxyd2 mutant mice is similar to that in wild-type, suggesting that Fxyd2 does not play a role in normal acute pain responses. Second, Fxyd2 mutation affects neither the establishment, nor the severity of the hyperalgesic state induced by SNI. Third, Fxyd2 function appears to be necessary to maintain the hypersensitivity of injured neurons in this neuropathic pain model.

Intrathecal injection of siRNA targeting the Fxyd2 mRNA in rats reduces pain behavior in an experimental model of neuropathic pain. Since the results from the analysis of Fxyd2 null mutant mice could potentially be explained by somatosensory defects that arose during development, we carried out acute knockdown of Fxyd2 gene function with a specific Fxyd2 siRNA combined with the SNI model of neuropathic pain. For these experiments we used rats since a siRNA shown to be effective against rat Fxyd2 mRNA has been published (Wetzel et al, 2004). Two groups of 6 adult male Sprague Dawley rats were tested: i) surgery; control siRNA and ii) surgery; Fxyd2 siRNA. The Randall-Stilletto test of mechanical sensitivity was used to calculate nociceptive thresholds. As shown in FIG. 2, from day 5 to day 8 after SNI, reduced nociceptive thresholds in operated animals demonstrated a chronic mechanical hypersensitivity (from 247.5 g to 127.5 g). Subsequently, Fxyd2 or control siRNA (2 µg) were injected intrathecally on post-surgery days 11, 12 and 13. On day 14, Fxyd2 siRNA injected animals displayed a marked increase up to 145 g in the nociceptive threshold, whereas in controls the thresholds further decreased to 102.5 g. On day 14, 1 µg of siRNA was injected and caused an increase of the nociceptive threshold to 152.5 g in Fxyd2 siRNA injected animals, compared to 92.5 g for the control. Injection of 1.6 µg of Fxyd2 siRNA on day 15 led to a further increase in nociceptive threshold to 165 g on day 16, at which time the control levels were 90.0 g.

These results show that acute intrathecal administration of Fxyd2 siRNA to rats in an experimental model of neuropathic pain caused dramatic reduction of the pain behavior, suggesting that Fxyd2 plays a role in maintaining hyperalgesia in this model.

Example 2

Materials and Methods

Real-Time qPCR

1 µg of total RNA from human DRGs (Clontech, Lot number 1105216A) or from human fibroblasts (provided by Dr. C. Angebault-Prouteau) were reverse-transcribed with 100 U of Superscript II reverse transcriptase (Invitrogen) and 5 µM hexamer random primers (Boehringer Mannheim), 0.5 mM of each dNTPs (Pharmacia), 10 mM of dithiothreitol and 20 U of recombinant RNase inhibitor (Promega) for 1 hour at 37° C. and then stored at −80° C. until use. Real time PCR was carried out as described previously (Elzière et al., 2014) using SYBR Green I dye detection on the LightCycler system (Roche Molecular Biochemichals). PCR reactions were performed in 96 well plates in a 10 µl volume containing 3 µl of RT product (final dilution 1/30), 0.5 µM of forward and reverse primers, and 2 µl of QuantiTect SYBR Green PCR Master Mix (Roche Diagnosis). Amplified products were sequenced at least once (Beckman Coulter Genomics, UK). The relative amounts of specifically amplified cDNAs were calculated using the delta-CT method (Hoebeeck et al., 2005; Vandesompele et al., 2002) on three independent experimental replicates and normalized by dividing with an appropriate normalization factor. This factor was Beta actin (ACTB) (Genbank: NM_001101.3); Human FXYD2 (GenBank:NM_001680) primers were purchased from Clinisciences (HP205498).

Immunohistochemistry.

Immunofluorescent staining was performed as previously described (Ventéo et al., 2012). Human lumbar DRGs were collected through the "Coordination Hospitalière de Prélèvement et Agence de Biomédecine" and harvested according to the French Biomedical Agency guidelines, from two brain-dead adult patients who were organ donors, as previously reported (Bauchet et al., 2013). Immunohistochemistry was performed using a mouse anti-FXYD2 antibody (Abnova, H00000486-M01) and the Vectastain ABC kit (Vector).

Results

The inventors assessed whether FXYD2 expression was conserved in human DRGs. First, by RT-qPCR analyses on human cDNA samples prepared from fibroblasts or lumbar DRGs, the inventors uncovered that FXYD2 was present at high levels specifically in the DRGs (FIG. 3A). In addition, by performing immunohistochemistry on human lumbar DRG sections, the inventors found that FXYD2 was strikingly detected in subpopulations of sensory neurons of small- and medium-diameters representing about 45% of the entire DRG neuronal population (FIG. 3B). Therefore, these results show that FXYD2 expression in primary sensory neuron subtypes has been evolutionary conserved.

REFERENCES

Throughout this application, various references describe the state of the art to which this invention pertains. The disclosures of these references are hereby incorporated by reference into the present disclosure.

Bauchet L, Lonjon N, Vachiery-Lahaye F, Boularan A, Privat A, Hugnot J P. 2013. Isolation and culture of precursor cells from the adult human spinal cord. Methods Mol Biol 1059: 87-93.

Chaplan S, Bach F, Pogrel J, Chung J, Yaksh T. (1994) Quantitative assessment of tactile allodynia in the rat paw. J Neurosci Methods 53:55-63.

Decosterd I, Woolf C J. (2000) Spared nerve injury: an animal model of persistent peripheral neuropathic pain. Pain 87(2): 149-58.

Elzière L. Sar C, Ventéo S, Bourane S, Puech S, Sonrier C, Boukhadaoui H, Fichard A, Pattyn A, Valmier J, Carroll P, Méchaly I. 2014. CaMKK-CaMK1a, a new post-traumatic signalling pathway induced in mouse somatosensory neurons. PLoS One 9: e97736.

Gegelashvili et al (2007). Glutamate transporter GLAST/EAAT1 directs cell surface expression of FXYD2/gamma subunit of Na,K-ATPase in human fetal astrocytes. Neurochemistry International 50; 916-920.

Hoebeeck J, van der Luijt R, Poppe B, De Smet E, Yigit N, Claes K, Zewald R, de Jong G J, De Paepe A, Speleman F, Vandesompele J. 2005. Rapid detection of VHL exon deletions using real-time quantitative PCR. Lab Invest 85: 24-33.

Jones D H, Li T Y, Arystarkhova E, Barr K J, Wetzel R K, Peng J, Marham K, Sweadner K J, Fong G-H, Kidder G M. (2005) Na,K-ATPase from mice lacking the □ subunit (FXYD2) exhibits altered Na affinity and decreased thermal stability. J Biol Chem 280: 19003-19011

Kayser V, Basbaum A I, Guilbaud G. (1990) Deafferentation in the rat increases mechanical nociceptive threshold in the innervated limbs. Brain Res 508: 329-32

Vandesompele J, Preter K, Pattyn F, Poppe B, Van Roy N, De Paepe A, Speleman F. 2002. Accurate normalization of real-time quantitative RT-PCR data by geometric averaging of multiple internal control genes. Genome Bio13: RESEARCH0034.

Ventéo S, Bourane S, Méchaly I, Sar C, Samad O, Puech S, Bolstein R, Valmier J, Pattyn A, Carroll P. (2012) Regulation of the Na,K-ATPase gamma-subunit FXYD2 by Runx1 and ret signalling in normal and injured non-peptidergic nociceptive sensory neurons. PlosOne 7(1): e29852

Wetzel R, Pascoa J, Arystarkhova E. (2004) Stress-induced expression of the □ subunit (FXYD2) modulates Na,K-ATPase activity and cell growth. J Biol Chem 279: 41750-41757

The invention claimed is:

1. A method for treating neuropathic pain in a patient in need thereof comprising the step of administering to said patient a therapeutically effective amount of an inhibitor of human FXYD domain containing ion transport regulator 2 (FXYD2) gene expression, wherein the sequence of the FXYD2 gene is as shown in Genbank Accession number NM_001680.4 (SEQ ID NO: 4) or NM_021603.3 (SEQ ID NO: 5).

2. The method according to claim 1, wherein said inhibitor is selected from the group consisting of siRNAs, shRNAs, antisense oligonucleotides and ribozymes.

3. The method according to claim 1, wherein the neuropathic pain is peripheral neuropathic pain.

4. The method according to claim 1, wherein the patient in need thereof is suffering from a disease selected from the group consisting of acute and chronic inflammatory demyelinating polyradiculoneuropathy; alcoholic polyneuropathy; chemotherapy-induced polyneuropathy; complex regional pain syndrome; an entrapment neuropathy; HfV sensory neuropathy; an iatrogenic neuralgia; idiopathic sensory neuropathy; nerve compression or infiltration by a tumor; nutritional deficiency-related neuropathies; painful diabetic neuropathy; phantom limb pain; postherpetic neuralgia; postradiation plexopathy; radiculopathy; toxic exposure-related neuropathies; tic douloureux (trigeminal neuralgia); and/or posttraumatic neuralgias.

5. The method of claim 4, wherein the entrapment neuropathy is carpal tunnel syndrome.

6. The method of claim 4, wherein the iatrogenic neuralgia is postmastectomy pain or postthoracotomy pain.

7. The method of claim 4, wherein the radiculopathy is cervical, thoracic, or lumbosacral.

* * * * *